US012653381B2

(12) United States Patent     (10) Patent No.:   US 12,653,381 B2

Li et al.                    (45) Date of Patent:     Jun. 16, 2026

(54) ENDOSCOPE DEVICE WITH OFF AXIS VIEW

(71) Applicant: ALTEK BIOTECHNOLOGY CORPORATION, Hsinchu City (TW)

(72) Inventors: Liang-Yi Li, Hsinchu City (TW); Chun-Wei Liu, Hsinchu City (TW)

(73) Assignee: ALTEK BIOTECHNOLOGY CORPORATION, Hsinchu City (TW)

( * ) Notice: Subject to any disclaimer, the term of this patent is extended or adjusted under 35 U.S.C. 154(b) by 534 days.

(21) Appl. No.: 18/139,366

(22) Filed: Apr. 26, 2023

(65) Prior Publication Data

US 2024/0358240 A1     Oct. 31, 2024

(51) Int. Cl.
*A61B 1/00*       (2006.01)

(52) U.S. Cl.
CPC .................................. *A61B 1/00179* (2013.01)

(58) Field of Classification Search
CPC .............. A61B 1/0008; A61B 1/00096; A61B 1/00105; A61B 1/00108; A61B 1/00117; A61B 1/00177; A61B 1/00179; A61B 1/00181; A61B 1/05; A61B 1/051; A61B 1/053; A61B 1/0607; A61B 1/0615; A61B 1/0623; A61B 1/0625; A61B 1/0669; A61B 1/07; H04N 23/51
See application file for complete search history.

(56) References Cited

U.S. PATENT DOCUMENTS

| | | | | |
|---|---|---|---|---|
| 4,868,644 | A * | 9/1989 | Yabe ...................... | H04N 23/54 600/109 |
| 5,633,675 | A * | 5/1997 | Danna .................. | A61B 1/0623 600/129 |
| 9,655,679 | B2 | 5/2017 | Desai | |
| 2007/0038031 | A1 * | 2/2007 | Miyagi .................... | A61B 1/07 600/156 |
| 2009/0043166 | A1 * | 2/2009 | Ishii ................... | A61B 1/00179 600/130 |

(Continued)

FOREIGN PATENT DOCUMENTS

| | | |
|---|---|---|
| CN | 104968255 A | 10/2015 |
| WO | 2013/047186 A1 | 4/2013 |

*Primary Examiner* — Michael J Carey
*Assistant Examiner* — Stephen Floyd London
(74) *Attorney, Agent, or Firm* — Winston Hsu

(57)          ABSTRACT

An endoscope device includes an operation processor and a detection module. The detection module is electrically connected with the operation processor. The detection module includes a tube, an optical transmission component, an optical detector, a signal transmission component, a first holder and a second holder. The optical transmission component has a first part and a second part bent to each other. The optical detector is located above the first part. The signal transmission component is coupled with the optical detector, and is parallel to the second part, and bent from a detection surface of the optical detector. The first holder includes a first accommodating structure adapted to accommodate the optical detector. The second holder includes a second accommodating structure adapted to accommodate the first part, and the optical transmission component and the optical detector are assembled between the first holder and the second holder to install inside the tube.

19 Claims, 5 Drawing Sheets

(56)                    References Cited

U.S. PATENT DOCUMENTS

| | | | | |
|---|---|---|---|---|
| 2012/0253121 A1* | 10/2012 | Kitano | ................ | A61B 1/0623 |
| | | | | 600/109 |
| 2013/0296885 A1 | 11/2013 | Desai | | |
| 2017/0112581 A1 | 4/2017 | Cohen | | |
| 2017/0168287 A1* | 6/2017 | Lietzau | .............. | G02B 23/2453 |
| 2019/0208143 A1* | 7/2019 | Brooks | ............. | A61B 1/00183 |
| 2019/0335068 A1* | 10/2019 | Kato | ........................ | A61B 1/07 |
| 2021/0068623 A1* | 3/2021 | Ichihara | ............. | A61B 1/00174 |
| 2021/0378496 A1* | 12/2021 | Kupferschmid | ... | A61B 1/00135 |
| 2022/0332021 A1* | 10/2022 | Hedemann | ........ | A61B 1/00179 |

* cited by examiner

10

Endoscope device

12    Operation processor    Detection module    14

14

16

30(24)

20

22

18A    18B

32(24)

18

ENDOSCOPE DEVICE WITH OFF AXIS VIEW

BACKGROUND OF THE INVENTION

1. Field of the Invention

The present invention relates to an endoscope device, and more particularly, to an endoscope device with off axis view.

2. Description of the Prior Art

An endoscope is the medical equipment that is inserted into the organism to observe condition of the internal organs. The detection camera of the endoscope is disposed on the front end of the pipeline; the planar normal vector of the detection surface of the conventional endoscope is parallel to the longitudinal direction of the pipeline of the endoscope, and the kind of endoscope has a drawback of inconvenient use. The conventional endoscope in another type has the planar normal vector of the detection surface that is bent from the longitudinal direction of the pipeline, which disposes the triangular prism in front of the detection camera to change the direction of light. However, the type of the endoscope needs the extra cost of the triangular prism, and further has the high-precision fixing structure configured to locate relative position between the triangular prism and the detection camera, which is expensive and easily damaged.

SUMMARY OF THE INVENTION

The present invention provides an endoscope device with off axis view for solving above drawbacks.

According to the claimed invention, an endoscope device includes an operation processor and a detection module. The detection module is electrically connected with the operation processor. The detection module includes a tube, an optical transmission component, an optical detector, a signal transmission component, a first holder and a second holder. The optical transmission component has a first part and a second part bent to each other, and a predefined included angle is formed between a structurally longitudinal direction of the second part and a structurally longitudinal direction of the first part. The optical detector is located above the first part. The signal transmission component is coupled with the optical detector, and has a structurally longitudinal direction parallel to the structurally longitudinal direction of the second part, and the predefined included angle is formed between the structurally longitudinal direction of the signal transmission component and a detection planar normal vector of the optical detector. The first holder includes a first accommodating structure adapted to accommodate the optical detector. The second holder includes a second accommodating structure adapted to accommodate the first part, and the optical transmission component and the optical detector are assembled between the first holder and the second holder to install inside the tube.

According to the claimed invention, the first holder further includes a plurality of accommodating surfaces adapted to respectively abut against a plurality of outer surfaces of the optical detector. The first holder further includes a plurality of abutting surfaces disposed adjacent to the first accommodating structure and adapted to abut against an upper surface of the optical transmission. The plurality of accommodating surfaces at least includes a first accommodating surface, a second accommodating surface and a third accommodating surface. The first accommodating surface is connected between the second accommodating surface and the third accommodating surface. The plurality of abutting surfaces is disposed adjacent to the second accommodating surface and the third accommodating surface, and a planar normal vector of each of the plurality of abutting surfaces is parallel to a planar normal vector of the first accommodating surface.

According to the claimed invention, the first holder further includes a first arc portion located on a position opposite to the plurality of abutting surfaces and adapted to abut against an inner surface of the tube. The first holder further includes a slotted portion formed on a position of the first arc portion adjacent to the signal transmission component, connection between the optical detector and the signal transmission component is located inside the slotted portion. The first holder further includes a first distally sectional portion connected between the first arc portion and the plurality of abutting surfaces, and adapted to align with a detection surface of the optical detector. An arc curvature of the first arc portion corresponds to an upper portion curvature of the inner surface.

According to the claimed invention, the second holder further includes a first holding portion, a second holding portion and a division portion, and the division portion is disposed between the first holding portion and the second holding portion to form the second accommodating structure, and two optical transmission portions of the optical transmission component are respectively located inside the first holding portion and the second holding portion. The second holder further includes a first holding arc surface and a second holding arc surface respectively set inside the first holding portion and the second holding portion and adapted to hold the two optical transmission portions. The second holder further includes an obliquely cutting portion disposed on an end of the division portion adjacent to the signal transmission component. The second holder further includes a second distally sectional portion disposed the other end of the division portion opposite to the obliquely cutting portion, and adapted to align with a detection surface of the optical detector.

According to the claimed invention, the second holder further includes a second arc portion disposed on a side of the second holder opposite to the first holder, and adapted to abut against an inner surface of the tube. An arc curvature of the second arc portion corresponds to a lower portion curvature of the inner surface.

According to the claimed invention, the second holder further includes a first slotted sectional portion and a second slotted sectional portion disposed on a side of the first holder adjacent to the signal transmission component, the second holder further includes a third slotted sectional portion disposed on a side of the second holder adjacent to the second part and adapted to align with the first slotted sectional portion and the second slotted sectional portion. The optical transmission component includes two optical transmission portions disposed side by side and adapted to clamp the signal transmission component, and each of the two optical transmission portions has the first part and the second part bent to each other.

According to the claimed invention, the second part has a first end and a second end opposite to each other, the first end is connected with the first part, the second end is extended out of or located inside the tube, and the detection module further comprises an optical emitter aligning with the second end. The predefined included angle is formed between the detection planar normal vector of the optical detector and a structurally longitudinal direction of the tube.

The endoscope device of the present application can provide the off axis view by connecting the optical detector with the signal transmission component in a bending manner, so as to form the predefined included angle, which may be equal to or close to thirty degrees, between the detection planar normal vector of the optical detector and the structurally longitudinal direction of the tube. An actual value of the predefined included angle is not limited to the foresaid embodiment, and can be varied in accordance with the design demand. The optical transmission component can be the fiber optic bundle or the light guide, and can have the first part and the second part bend from each other due to a structural feature of the optical detector and the signal transmission component. The optical transmission component can preferably include two optical transmission portions used to clamp the signal transmission component and the division portion of the second holder. Dimensions of assembly of the first holder and the second holder can correspond to the size of the tube for tight match. The optical transmission component, the optical detector and the signal transmission component can be covered and fixed by the first holder and the second holder to assemble with the tube for accomplishing the endoscope device.

These and other objectives of the present invention will no doubt become obvious to those of ordinary skill in the art after reading the following detailed description of the preferred embodiment that is illustrated in the various figures and drawings.

DETAILED DESCRIPTION

Figure 1:
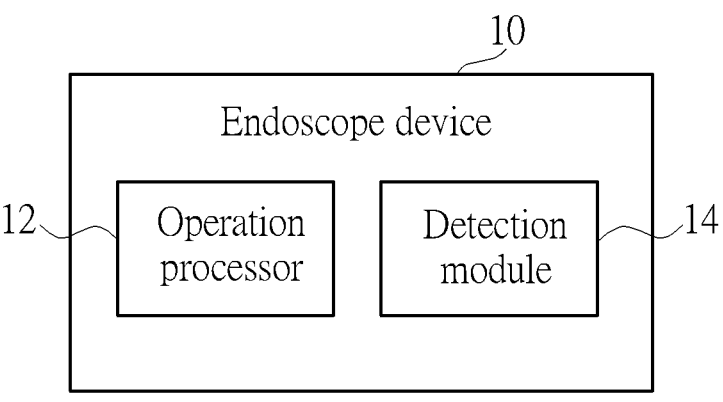
FIG. 1 is a functional block diagram of an endoscope device according to an embodiment of the present application.
Figure 2:
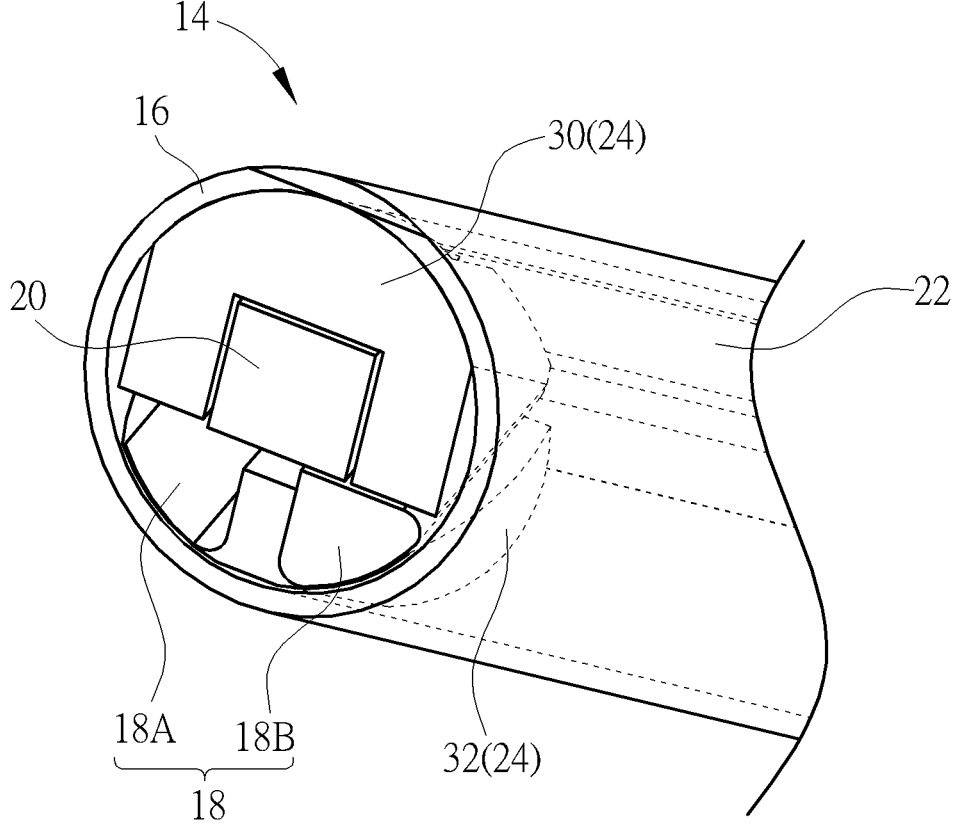
FIG. 2 is an assembly diagram of a part of the endoscope device according to the embodiment of the present application.

Please refer to FIG. 1 and FIG. 2. FIG. 1 is a functional block diagram of an endoscope device 10 according to an embodiment of the present application. FIG. 2 is an assembly diagram of a part of the endoscope device 10 according to the embodiment of the present application. The endoscope device 10 is the medical equipment, which utilizes an optical image technology to acquire and analyze biological information. The endoscope device 10 can include an operation processor 12 and a detection module 14 capable of communicating with each other in a wire manner or in a wireless manner. The operation processor 12 may be a built-in unit of the detection module 14, or an independent unit electrically connected with the detection module 14, or a cloud unit communicated with the detection module 14 in remote connection. Application of the operation processor 12 can depend on a design demand. The detection module 14 can acquire a detection image via the optical image technology. The operation processor 12 can receive and analyze the detection image, and then output the processed detection image or a related control command in accordance with an analysis result.

Figure 3:
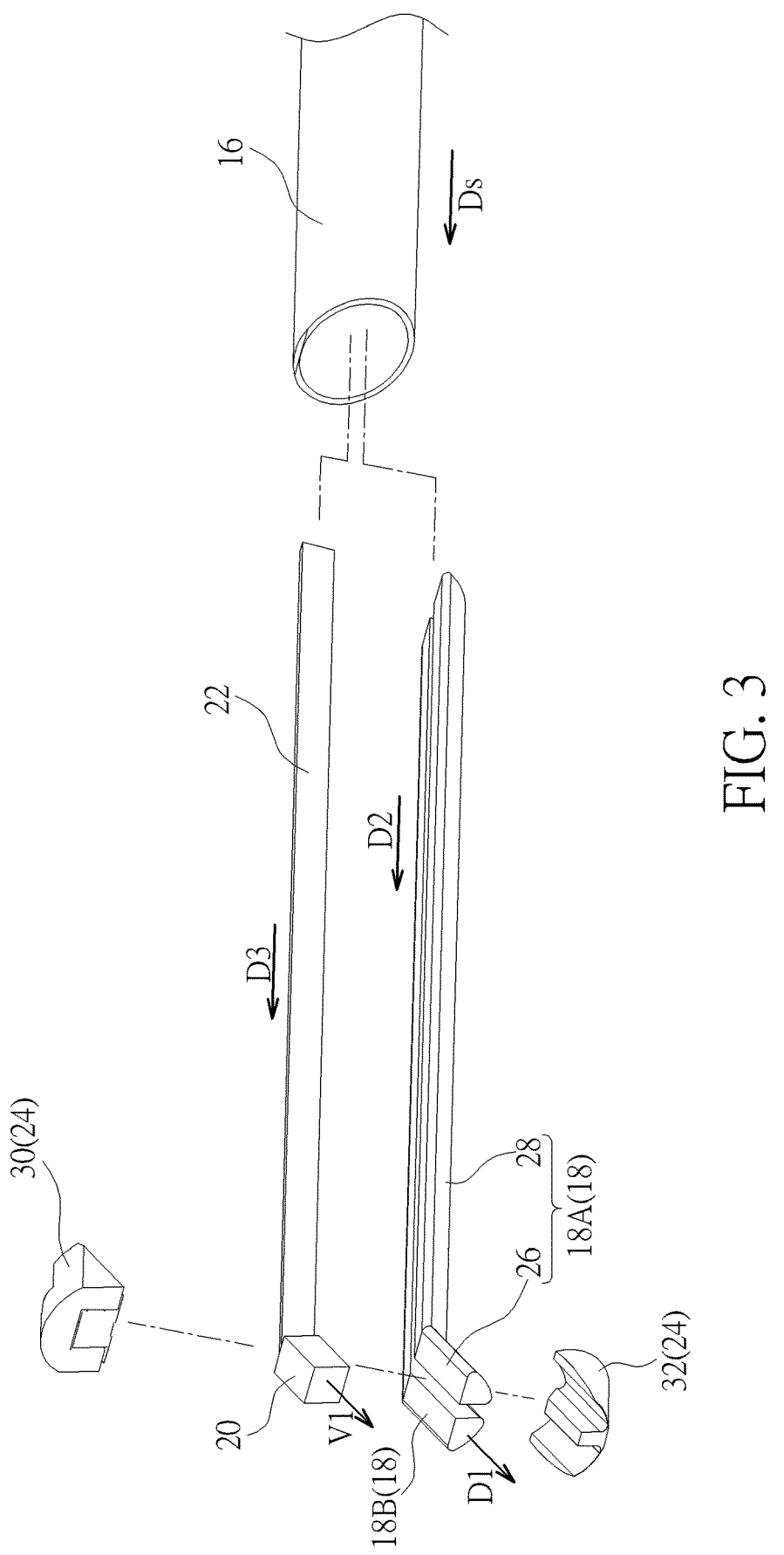
FIG. 3 and FIG. 4 are exploded diagrams of a detection module in different views according to the embodiment of the present application.
Figure 4:
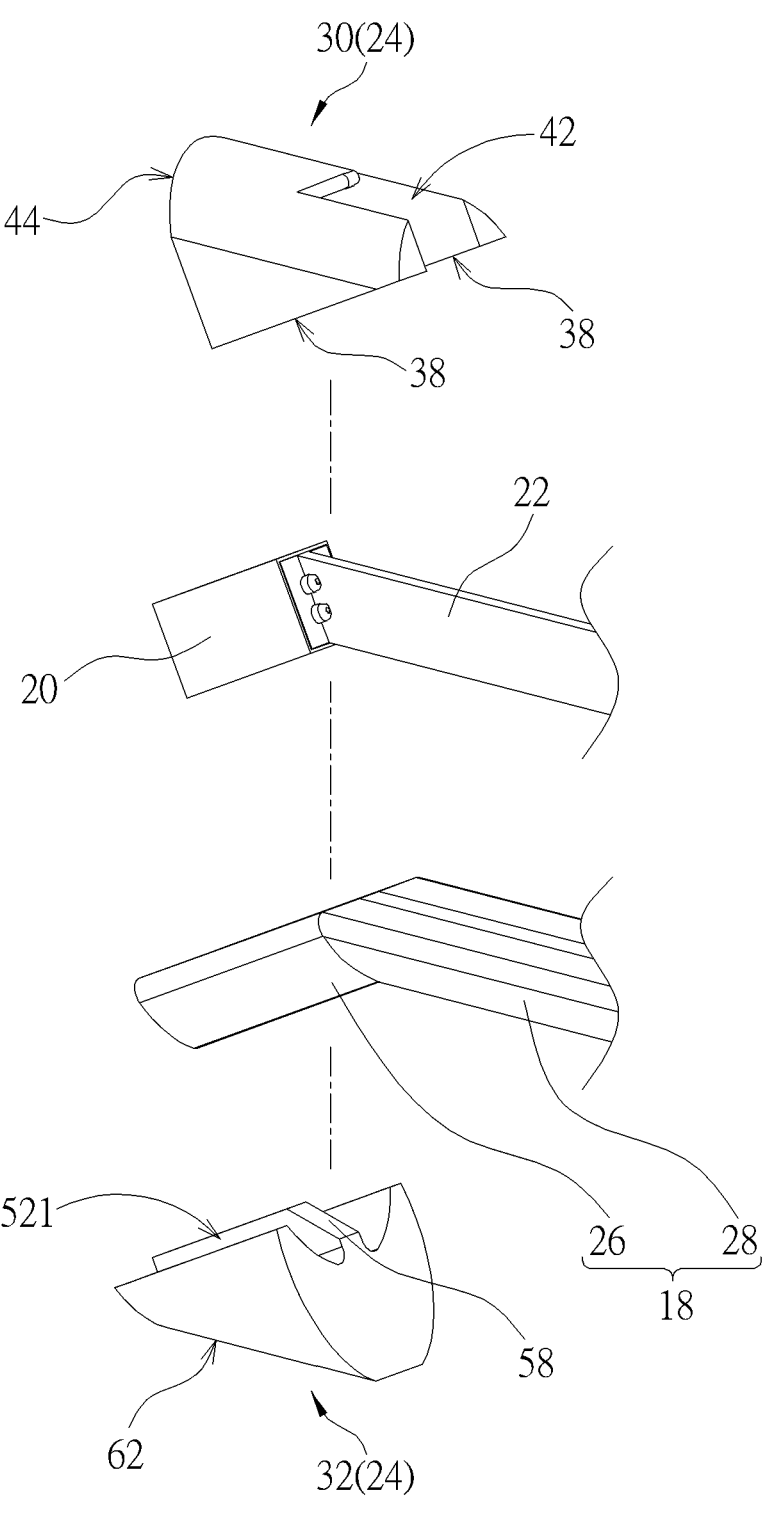
Figure 5:
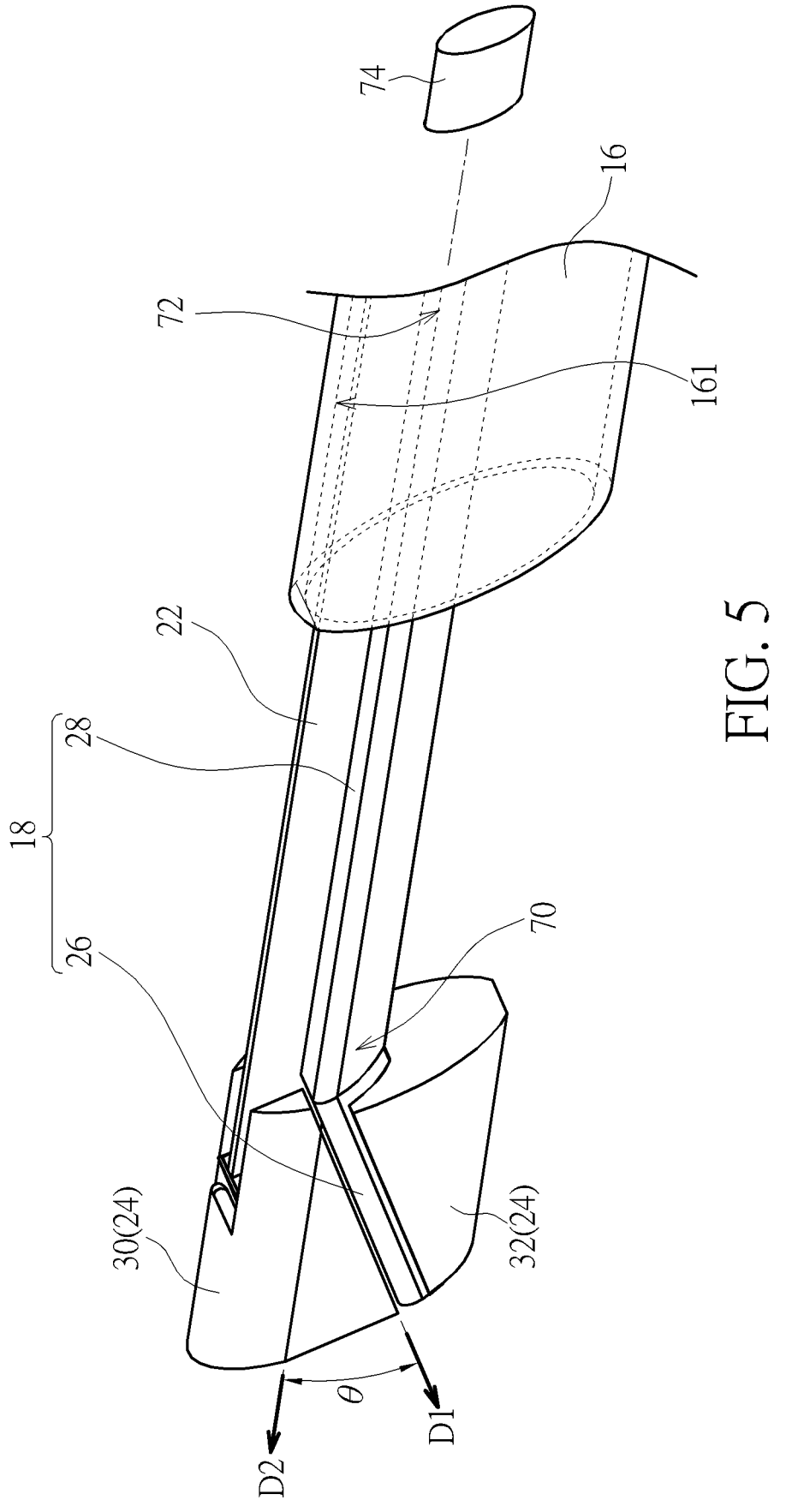
FIG. 5 is a diagram of a part of the detection module according to the embodiment of the present application.

Please refer to FIG. 2 to FIG. 5. FIG. 3 and FIG. 4 are exploded diagrams of the detection module 14 in different views according to the embodiment of the present application. FIG. 5 is a diagram of a part of the detection module 14 according to the embodiment of the present application. The detection module 14 can include a tube 16, an optical transmission component 18, an optical detector 20, a signal transmission component 22 and a holding assembly 24. The tube 16 can be made by hard material or deformable material, such as the hard tube made by metal or the deformable tube made by rubber. The tube 16 can cover inner components of the detection module 14 for waterproof and dustproof protection. In the embodiment, the optical transmission component 18 can include two optical transmission portions 18A and 18B. Each of the optical transmission portions 18A and 18B can include a first part 26 and a second part 28 bent from each other. A predefined included angle θ can be formed between a structurally longitudinal direction D1 of the first part 26 and a structurally longitudinal direction D2 of the second part 28. The two optical transmission portions 18A and 18B can be arranged side by side to clamp the signal transmission component 22.

The optical detector 20 can be coupled to the signal transmission component 22. The optical detector 20 can be disposed on the first part 26 of the optical transmission component 18, and the signal transmission component 22 can be disposed on the second part 28 of the optical transmission component 18. Therefore, a detection planar normal vector V1 of the optical detector 20 can be parallel to or substantially parallel to the structurally longitudinal direction D1 of the first part 26, and a structurally longitudinal direction D3 of the signal transmission component 22 can be parallel to or substantially parallel to the structurally longitudinal direction D2 of the second part 28. Accordingly, the predefined included angle θ can be formed between the structurally longitudinal direction D3 of the signal transmission component 22 and the detection planar normal vector V1 of the optical detector 20. The tube 16 can be a straight structure, so that a structurally longitudinal direction Ds of the tube 16 can be parallel to or substantially parallel to the structurally longitudinal direction D2 of the second part 28 and the structurally longitudinal direction D3 of the signal transmission component 22, and the predefined included angle θ can be formed between the structurally longitudinal direction Ds and the detection planar normal vector V1.

The holding assembly 24 can fix the optical transmission component 18, the optical detector 20 and the signal transmission component 22 inside the tube 16. In the embodiment, the holding assembly 24 can include a first holder 30 and a second holder 32 separated from each other. The optical transmission component 18 and the optical detector 20 can be clamped by the first holder 30 and the second holder 32. The top end of the optical detector 20 can be pressed by the first holder 30, and the bottom end of the optical transmission component 18 can be held by the second holder 32. When the optical transmission component 18 and the optical detector 20 are fixed by the first holder 30 and the second holder 32, any component, such as a strap, glue or a latch, can be used to attach the first holder 30 to the second holder 32 for avoiding separation, or the holding assembly 24 can be directly put into the tube 16 for constraint. In other possible embodiments, the first holder 30 may be monolithically integrated with the second holder 32. Any holding structure capable of fixing the optical transmission component 18 and the optical detector 20 can belong to a design scope in the holding assembly 24 of the present application.

Figure 6:
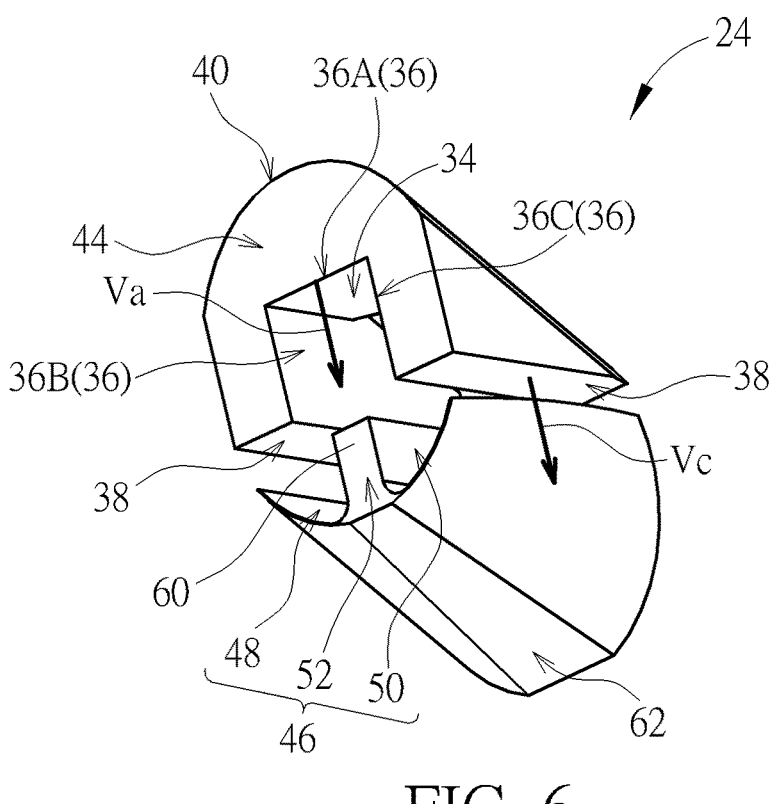
FIG. 6 and FIG. 7 are structural diagrams of a holding assembly in different views according to the embodiment of the present application.
Figure 7:
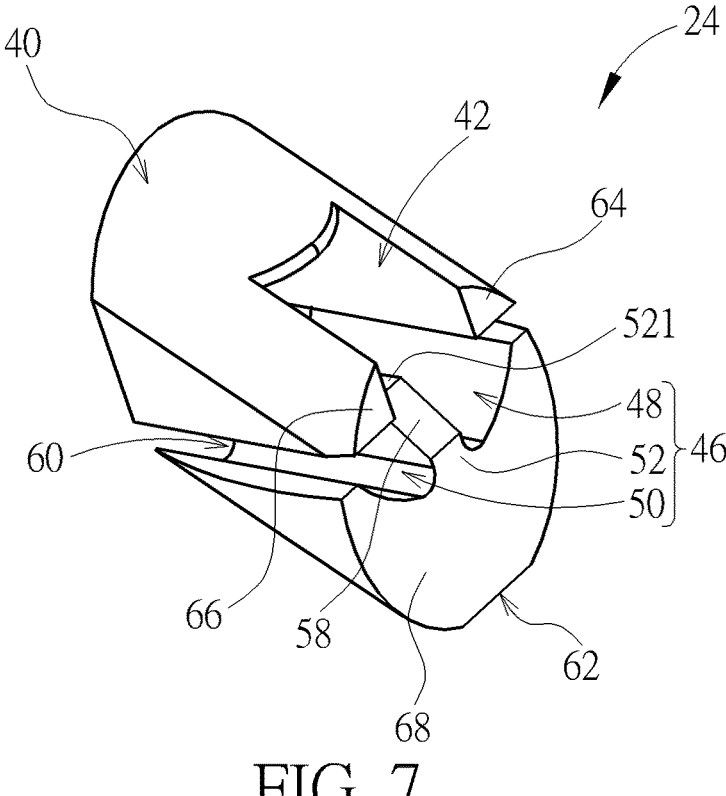

Please refer to FIG. 2 to FIG. 7. FIG. 6 and FIG. 7 are structural diagrams of the holding assembly 24 in different views according to the embodiment of the present application. The first holder 30 can include a first accommodating structure 34, several accommodating surfaces 36, several abutting surfaces 38, a first arc portion 40, a slotted portion 42 and a first distally sectional portion 44. The optical detector 20 can be accommodated inside the first accommodating structure 34. The accommodating surfaces 36 can be inner surfaces of the first accommodating structure 34, and respectively abut against outer surfaces of the optical detector 20. The abutting surfaces 38 can be some part of outer surfaces of the first accommodating structure 34. The accommodating surfaces 36 can at least include a first accommodating surface 36A, a second accommodating surface 36B and a third accommodating surface 36C. The first accommodating surface 36A can be connected between the second accommodating surface 36B and the third accommodating surface 36C, so as to form the first accommodating structure 34. The abutting surfaces 38 can be disposed adjacent to the second accommodating surface 36B and the third accommodating surface 36C of the first accommodating structure 34, and can abut against an upper surface of the optical transmission component 18. A planar normal vector Vc of the abutting surface 38 can be parallel to or substantially parallel to a planar normal vector Va of the first accommodating surface 36A.

Besides, position of the first arc portion 40 can correspond to the abutting surface 38, and the first arc portion 40 can abut against an inner surface 161 of the tube 16. The slotted portion 42 can be formed on position of the first arc portion 40 adjacent to the signal transmission component 22. A coupling joint between the optical detector 20 and the signal transmission component 22 can be located inside the slotted portion 42. The first distally sectional portion 44 can be connected between the first arc portion 40 and the abutting surface 38, and align with a detection surface of the optical detector 20. The foresaid detection surface can be interpreted as a surface where on the detection planar normal vector V1 is based. Therefore, the first arc portion 40 can be formed on the top of the first holder 30 to match with an aperture of the tube 16, and an arc curvature of the first arc portion 40 can correspond to an upper portion curvature of the inner surface 161 of the tube 16; the bottom of the first holder 30 can utilize the abutting surface 38 to tightly abut against the second holder 32. Space between the top and the bottom of the first holder 30 can form a chamber to be designed as the first accommodating structure 34, and the accommodating surfaces 36 can tightly abut against the optical detector 20. The rear edge of the first holder 30 can have the slotted portion 42, so that the coupling joint between the optical detector 20 and the signal transmission component 22 can be set inside the slotted portion 42.

The second holder 32 can include a second accommodating structure 46, a first holding portion 48, a second holding portion 50, a division portion 52, a first holding arc surface 54, a second holding arc surface 56, an obliquely cutting portion 58, a second distally sectional portion 60 and a second arc portion 62. The first part 26 of the optical transmission component 18 can be accommodated inside the second accommodating structure 46. The second accommodating structure 46 can be formed by the first holding portion 48, the second holding portion 50 and the division portion 52. The division portion 52 can be disposed between the first holding portion 48 and the second holding portion 50. The first holding arc surface 54 and the second holding arc surface 56 can be respectively located inside the first holding portion 48 and the second holding portion 50, and used to hold the optical transmission portions 18A and 18B of the optical transmission component 18. Thus, the optical transmission portions 18A and 18B can be respectively disposed inside the first holding portion 48 and the second holding portion 50, and the division portion 52 can be set between the optical transmission portions 18A and 18B.

Moreover, the obliquely cutting portion 58 can be disposed on an end of the division portion 52 adjacent to the signal transmission component 22; because the optical detector 20 is bent from the signal transmission component 22 to form the predefined included angle θ, the coupling joint between the optical detector 20 and the signal transmission component 22 is not structurally interfered with the second holder 32 due to design of the obliquely cutting portion 58. A top surface 521 of the division portion 52 can be connected to and bent from the obliquely cutting portion 58. The top surface 521 and the obliquely cutting portion 58 can respectively abut against the first part 26 and the second part 28 of the optical transmission component 18. The second distally sectional portion 60 can be disposed on the other end of the division portion 52 opposite to the obliquely cutting portion 58, and align with the detection surface of the optical detector 20. The foresaid detection surface can be interpreted as the surface where on the detection planar normal vector V1 is based. The second arc portion 62 can be disposed on a side of the second holder 32 opposite to the first holder 30, and used to abut against the inner surface 161 of the tube 16. Therefore, the second arc portion 62 can be formed on the bottom of the second holder 32 to match with the aperture of the tube 16, and an arc curvature of the second arc portion 62 can correspond to a lower portion curvature of the inner surface 161 of the tube 16. The top end of the second holder 32 can abut against the first holder 30, so that the top surfaces of lateral walls of the first holding portion 48 and the second holding portion 50 can contact the abutting surfaces 38 of the first holder 30 for tight match. Space between the top and the bottom of the second holder 32 can have a chamber to dispose the division portion 52 between the first holding portion 48 and the second holding portion 50, so as to form the second accommodating structure 46. The rear end of the division portion 52 can dispose the obliquely cutting portion 58, and the division portion 52 is not structurally interfered with the coupling joint between the optical detector 20 and the signal transmission component 22 due to the obliquely cutting portion 58.

The first holder 30 can further include a first slotted sectional portion 64 and a second slotted sectional portion 66, respectively disposed on different position on a side of the first holder 30 adjacent to the signal transmission component 22. The first slotted sectional portion 64 and the second slotted sectional portion 66 can be connected to the abutting surfaces 38, and further disposed on the rear end of the first holder 30 opposite to the first distally sectional portion 44. The second holder 32 can further include a third slotted sectional portion 68 disposed on a side of the second holder 32 adjacent to the second part 28, and align with the first slotted sectional portion 64 and the second slotted sectional portion 66. The third slotted sectional portion 68 can be formed on the rear end of the second holder 32 opposite to the second distally sectional portion 60. It should be mentioned that the third slotted sectional portion 68 aligning with the first slotted sectional portion 64 and the second slotted sectional portion 66 can be interpreted as the first slotted sectional portion 64, the second slotted sectional portion 66 and the third slotted sectional portion 68 belong to the same plane when the first holder 30 is assembled with the second holder 32, or further interpreted as the first slotted sectional portion 64, the second slotted sectional portion 66 and the third slotted sectional portion 68 can have the same or similar planar normal vectors.

As shown in FIG. 5, the optical detector 20 can be held by the first part 26 of the optical transmission component 18; the front end of the first part 26 can point toward an opening of the tube 16 to provide an illumination beam, and the rear end of the first part 26 can be connected with the second part 28. The second part 28 can include a first end 70 and a second end 72 opposite to each other; the first end 70 can be connected with the first part 26, and the second end 72 can be extended out of the tube 16 or still set inside the tube 16. The second end 72 can point toward an optical emitter 74 of the detection module 14, and used to receive the illumination beam emitted by the optical emitter 74. The illumination beam can be transmitted out of the front end of the first part 26 through the total internal reflection of the optical transmission component 18 for illuminating an object; that is to say, the optical emitter 74 can be optionally disposed inside or outside the tube 16, which depends on the design demand.

In conclusion, the endoscope device of the present application can provide the off axis view by connecting the optical detector with the signal transmission component in a bending manner, so as to form the predefined included angle, which may be equal to or close to thirty degrees, between the detection planar normal vector of the optical detector and the structurally longitudinal direction of the tube. An actual value of the predefined included angle is not limited to the foresaid embodiment, and can be varied in accordance with the design demand. The optical transmission component can be the fiber optic bundle or the light guide, and can have the first part and the second part bend from each other due to a structural feature of the optical detector and the signal transmission component. The optical transmission component can preferably include two optical transmission portions used to clamp the signal transmission component and the division portion of the second holder. Dimensions of assembly of the first holder and the second holder can correspond to the size of the tube for tight match. The optical transmission component, the optical detector and the signal transmission component can be covered and fixed by the first holder and the second holder to assemble with the tube for accomplishing the endoscope device.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. An endoscope device, comprising:
an operation processor; and
a detection module electrically connected with the operation processor, the detection module comprising:
a tube;
an optical transmission component having a first part and a second part bent to each other, a predefined included angle being formed between a structurally longitudinal direction of the second part and a structurally longitudinal direction of the first part;
an optical detector located above the first part;
a signal transmission component coupled with the optical detector, having a structurally longitudinal direction parallel to the structurally longitudinal direction of the second part, and the predefined included angle being formed between the structurally longitudinal direction of the signal transmission component and a detection planar normal vector of the optical detector;
a first holder, comprising a first accommodating structure being a first chamber configured to accommodate the optical detector; and
a second holder, comprising a second accommodating structure being a second chamber, two opposite ends of the first part respectively being embedded into the second chamber and abutting against the optical detector, the optical transmission component and the optical detector being assembled between the first holder and the second holder to install inside the tube.

2. The endoscope device of claim 1, wherein the first holder further comprises a plurality of accommodating surfaces adapted to respectively abut against a plurality of outer surfaces of the optical detector.

3. The endoscope device of claim 2, wherein the first holder further comprises a plurality of abutting surfaces disposed adjacent to the first accommodating structure and adapted to abut against an upper surface of the optical transmission component.

4. The endoscope device of claim 3, wherein the plurality of accommodating surfaces comprises a first accommodating surface, a second accommodating surface and a third accommodating surface, the first accommodating surface is connected between the second accommodating surface and the third accommodating surface, the plurality of abutting surfaces is disposed adjacent to the second accommodating surface and the third accommodating surface, a planar normal vector of each of the plurality of abutting surfaces is parallel to a planar normal vector of the first accommodating surface.

5. The endoscope device of claim 3, wherein the first holder further comprises a first arc portion located on a position opposite to the plurality of abutting surfaces and adapted to abut against an inner surface of the tube.

6. The endoscope device of claim 5, wherein the first holder further comprises a slotted portion formed on a position of the first arc portion adjacent to the signal transmission component, connection between the optical detector and the signal transmission component is located inside the slotted portion.

7. The endoscope device of claim 5, wherein the first holder further comprises a first distally sectional portion connected between the first arc portion and the plurality of abutting surfaces, and adapted to align with a detection surface of the optical detector.

8. The endoscope device of claim 5, wherein an arc curvature of the first arc portion corresponds to an upper portion curvature of the inner surface.

9. The endoscope device of claim 1, wherein the second holder further comprises a first holding portion, a second holding portion and a division portion, the division portion is disposed between the first holding portion and the second holding portion to form the second accommodating structure, two optical transmission portions of the optical transmission component are respectively located inside the first holding portion and the second holding portion.

10. The endoscope device of claim 9, wherein the second holder further comprises a first holding arc surface and a second holding arc surface respectively set inside the first holding portion and the second holding portion and adapted to hold the two optical transmission portions.

11. The endoscope device of claim 9, wherein the second holder further comprises an obliquely cutting portion disposed on an end of the division portion adjacent to the signal transmission component.

12. The endoscope device of claim 11, wherein the second holder further comprises a second distally sectional portion disposed the other end of the division portion opposite to the obliquely cutting portion, and adapted to align with a detection surface of the optical detector.

13. The endoscope device of claim 1, wherein the second holder further comprises a second arc portion disposed on a side of the second holder opposite to the first holder, and adapted to abut against an inner surface of the tube.

14. The endoscope device of claim 13, wherein an arc curvature of the second arc portion corresponds to a lower portion curvature of the inner surface.

15. The endoscope device of claim 1, wherein the second first holder further comprises a first slotted sectional portion and a second slotted sectional portion disposed on a side of the first holder adjacent to the signal transmission component, the second holder further comprises a third slotted sectional portion disposed on a side of the second holder adjacent to the second part and adapted to align with the first slotted sectional portion and the second slotted sectional portion.

16. The endoscope device of claim 1, wherein the optical transmission component comprises two optical transmission portions disposed side by side and adapted to clamp the signal transmission component, each of the two optical transmission portions has the first part and the second part bent to each other.

17. The endoscope device of claim 1, wherein the second part has a first end and a second end opposite to each other, the first end is connected with the first part, the second end is extended out of the tube, and the detection module further comprises an optical emitter aligning with the second end.

18. The endoscope device of claim 1, wherein the second part has a first end and a second end opposite to each other, the first end is connected with the first part, the second end is located inside the tube, and the detection module further comprises an optical emitter aligning with the second end.

19. The endoscope device of claim 1, wherein the predefined included angle is formed between the detection planar normal vector of the optical detector and a structurally longitudinal direction of the tube.

* * * * *